(12) United States Patent
Bäuerlein et al.

(10) Patent No.: US 6,251,365 B1
(45) Date of Patent: Jun. 26, 2001

(54) SPECIFIC MAGNETOSOME, METHOD FOR THE PRODUCTION AND USE THEREOF

(75) Inventors: Edmund Bäuerlein, München; Dirk Schüler, Stassfurt; Regina Reszka, Schwanebeck; Sabine Päuser, Berlin, all of (DE)

(73) Assignee: Max-Delbruck-Centrum fur Molekulare Medizin and Max-Planck-Gesellschaft zur Forderung der Wissenschaften E.V. (DE)

( * ) Notice: Subject to any disclaimer, the term of this patent is extended or adjusted under 35 U.S.C. 154(b) by 0 days.

(21) Appl. No.: 09/397,705

(22) Filed: Sep. 1, 1999

(30) Foreign Application Priority Data

Mar. 7, 1997 (DE) .............................. 197 09 322

(51) Int. Cl.$^7$ ............... A61B 5/55; A61B 9/127
(52) U.S. Cl. ............... 424/9.3; 424/9.1; 424/9.2; 424/9.321; 424/9.34; 424/130.1; 424/450
(58) Field of Search ............... 424/9.1, 9.2, 9.3, 424/9.321, 9.34, 130.1

(56) References Cited

U.S. PATENT DOCUMENTS 4,677,067 * 6/1987 Schwartz et al. .................... 435/177
6,033,878 * 3/2000 Matsunaga .......................... 435/69.7

OTHER PUBLICATIONS

CA vol. 109 (1988), 176338x.
CA vol. 127 (1997), 146865y.
O. Schuler: Iron Transport, etc., J. Phys IV. France 7 (1997).
CA vol. 108 (1997), 18944.
CA vol. 108 (1997), 19036.
CA vol. 108 (1997), 128197.
CA vol. 116 (1997), 37865.
CA vol. 109 (1997), 176329.
Matsunaga, T., Magnetic Bacteria, Nippon Oyo Jiki Gakkaishi (1991), 15(4), 754–758.*
Miller, N., et al. Targeted Vectors for Gene Therapy, The Faseb Journal, vol. 9, Feb. 1995.*

* cited by examiner

Primary Examiner—Deborah J. R. Clark
Assistant Examiner—Eleanor Sorbello
(74) Attorney, Agent, or Firm—Gabriel P. Katona L.LP.

(57) ABSTRACT

A magnetosome comprising a magnetite monocrystal having a maximum diameter of 45 nm surrounded by a phospholipid membrane.

15 Claims, 1 Drawing Sheet

BEFORE     5 MINS. LATER

24 HRS. LATER     48 HRS. LATER

SPECIFIC MAGNETOSOME, METHOD FOR THE PRODUCTION AND USE THEREOF

Figure 1:
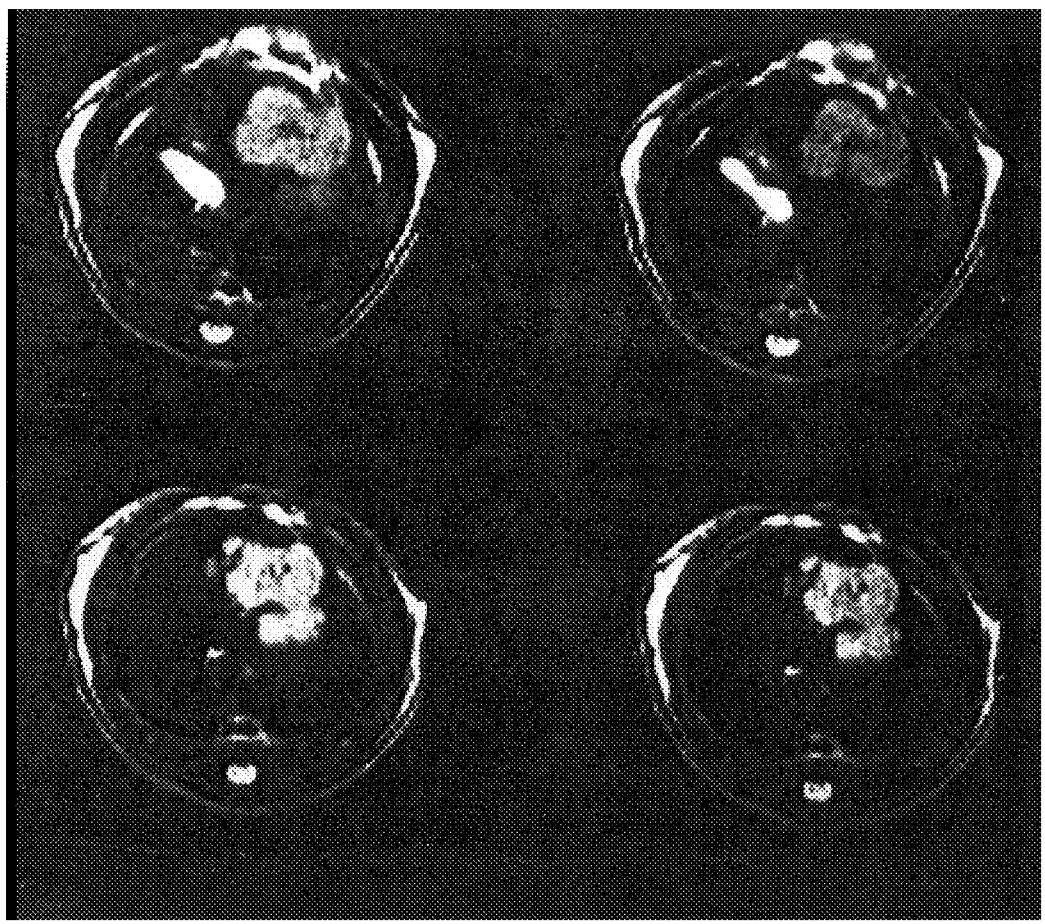

The invention relates to specific magnetosomes with magnetic particles of maximally 43–45 nm, method for the production and use thereof. Furthermore, it relates to magnetoliposomes which can be obtained from the said magnetosomes by liposomal encapsulation.

Fields of application of the invention are medicine and pharmaceutical industry.

It is known that superparamagnetic iron particles are applied in medical diagnostics as NMR contrast agents or in the form of immunoconjugates or as synthetic drug carriers. Matsunaga et al. described in 1989 magnetosomes obtained from the magnetic bacterium Magnetospirillum spec. ABMI (JP7-241192-A) and their use. However, these magnetosomes have the disadvantage that they are comparatively large, thus bringing about the danger that they may cause embolisms in medical use.

That is why it was the task of the invention to provide specific magnetosomes which are smaller than those known, thus
- improving their medical use as regards reaching the envisaged targets in the body of the patient and
- at the same time diminishing the danger of embolisms.

It was detected that magnetosomes with magnetic particles <50 nm are contained in the bacterium *Magnetospirillum gryphiswaldense*.

To our surprise, it was possible to produce these specific magnetosomes of the magnetic bacterium *Magnetospirillum gryphiswaldense* on a semi-industrial scale.

Accordingly, the object of the invention are the magnetosomes themselves, the method of production/preparation and use thereof, preferably in medicine and pharmacy.

The invention is implemented according to the claims.

According to the invention magnetosomes are characterized by a magnetic oxide magnetite $Fe_3O_4$ monocrystal with a maximum diameter of 43–45 nm surrounded by a phospholipid membrane. As a rule, they have a cubooctahedral shape.

The membrane consists preferably of phosphatidyl ethanolamine, phosphatidyl glycerol and phosphatidyl choline containing mainly the fatty acids palmitic acid, palmitoleic acid and oleic acid. The membrane consists preferably of 53±6% phosphatidyl ethanolamine, 38±6% phosphatidyl glycerol and 8.9±5% phosphatidyl choline where mainly the fatty acids palmitic acid (approx. 18.4%), palmitoleic acid (approx. 25.6%) and oleic acid (approx. 45.9%) are to be found.

A preferred variant of execution contains the magnetosomes as chains up to 100, preferably 10–60 magnetosomes and with a cationic surface charge. This chain form of magnetosomes increases the probability that antibodies and therapeutic agents may be correctly bound to them and become effective.

In addition, magnetosomes are also magnetosomes with additionally covalently bound antibodies or therapeutic agents bound to the magnetosome membrane through respective reactive groups.

Apart from that, the invention relates to a method for the production of these new magnetosomes. They are isolated from the magnetic bacterium *Magnetospirillum gryphiswaldense* according to a new fermentation method. For this purpose a new simple culture medium consisting of 0.3 g of $KH_2PO_4$, 1 g of Na acetate, 1 g of soybean peptone (Merck), 0.1 g of $NH_4Cl$, 0.1 g of yeast extract, pH 6.9 which does not contain a complexing agent for iron is preferably used. The concentration of oxygen in the medium is maintained below 2%, later Na acetate and $FeSO_4$ are added. After approx. 30 hours the magnetic cells may be gathered. After subjecting the cells to a lysis the magnetosomes are obtained in a high output according to a new method by separating them from cell fragments and cell sap in a magnetic separation column by means of a strong, powerful permanent magnet (Sm-Neodyn) and purifying them by washing.

Furthermore, magnetosomes according to the invention which are available packed in liposomes, forming themselves liposomes with other lipids or bound to the surface of liposomes are object of the invention. Such liposomes are
- so-called classical liposomes (MLV, SUV, LUV)
- so-called "stealth" liposomes (PEG)
- micellar systems (e.g. SDS, triton, sodium cholate)
- immunoliposomes containing e.g. antibodies or fab fragments against antigenes associated with diseases or adhesion molecules bound to the surface of the liposomes
- so-called cationic liposomes (DAC-Chol, DOCSPER)
- so-called fusogenic liposomes (reconstituted fusion proteins in liposomes).

Magnetoliposomes are prepared according to liposome preparation methods known per se, e.g. described in DE 41 34 158, DE 44 30 593, DE 44 46 937 and DE 196 31 189 with the magnetosomes being preferably added to the initial lipids.

The preferred modifications of magnetoliposomes and magnetosomes belonging to the invention are represented in Table 1 hereinafter.

TABLE 1

| | | | | Magnetoliposomes | | | |
|---|---|---|---|---|---|---|---|
| classical | "stealth" | immuno | cationic e.g. | fusiogenic e.g. | | | Magnetosomes |
| MLV | PEG | anti-CEA | DAC Chol/DOPE | HN, F protein | Immuno | | Gener, or antisense oligonucleotide |
| SUV | | anti Thy1.1 | SP Chol/DOPE | (Sendai virus) | anti CEA | | or ribozyme modified |
| LUV | | anti CD44 | DAC-Quat. | -> [pH 7] | anti CD44 | | |
| (REV) | | anti CD54 | Chol/DOPE | synthetic | anti CD 54, CD56 | | |
| | | anti CD56 | DECSPER | fusion | anti CD30 | | |
| | | anti CD30 | | proteins | | | |

TABLE 1-continued

| | | | Magnetoliposomes | | |
|---|---|---|---|---|---|
| classical | "stealth" | immuno | cationic e.g. | fusiogenic e.g. | Magnetosomes |
| | | anti CD31 | | HA influenza virus [pH 5,2] "cochelates" | |

The magnetosomes and magnetoliposomes according to the invention may contain specific antibodies additionally chemically coupled to their surfaces, one or a few therapeutic agents and radionuclides enclosed, i.e. encapsulated.

In addition, they, together with genetic material such e.g. plasmids, therapy genes, antisense oligonucleotides, ribozymes or gene diagnostic agents, may form cationic complexes suited for the transfer of genes.

These magnetosomes and magnetoliposomes according to the invention have a comprehensive spectrum of application. Owing to their magnetic properties they are per se (also unmodified) used as contrast agents for NMR examinations and as markers for mapping magnetic susceptibilities by means of a SQUID biomagnet meter and also as diagnostic agents for the detection of various diseases and focuses of inflammation or therapeutic agents as e. g. for purging ("taking out diseased cells"), as diagnostic agents for tumoral diseases or in lymphography, for inflammatory processes, for multiple sclerosis, Alzheimer disease and for Parkinson's disease or as a therapeutic agent against tumoral diseases, inflammatory processes and metabolic diseases.

Diagnostic agents are used preferably in the form of immunomagnetosomes or immunomagnetoliposomes. For this, antibodies or fab fragments against antigenes associated with diseases or adhesion molecules or ligands are covalently coupled to the magnetosome and magnetoliposome membrane through respective groups, preferably to phosphatidyl ethanolamine contained in the membrane through spacers of a differing length.

In particular, they are used as diagnostic agents for the detection of tumoral diseases or in lymphography, with among others anti CEA, anti CD44 being coupled to the magnetosome membrane or magnetoliposome membrane as a reagent. These antibody coupling products are also suited for detecting inflammatory processes such as arthroses (preferably with anti CD54, anti CD56) or for detecting multiple sclerosis or Alzheimer disease (preferably anti-β-amyloid, anti APOE4), Hogkin lymphoma cells (preferably with anti CD30) and Parkinson's disease.

The magnetosomes according to the invention are excellently suited for the so-called diagnostic applications.

It is necessary to use magnetoliposomes to simultaneously bring a therapeutic substance in relevant quantities to the target place. They are not only suited for coupling but also for enclosing therapeutic agents. In the case of magnetosomes therapeutic agents may be coupled only with a spacer being interconnected.

According to the invention an essential possibility of use is that therapeutic agents are coupled (magnetosomes) or coupled or enclosed (magnetoliposomes). These therapeutic agents may be enclosed in the membrane or in the aqueous interior of the liposomes depending on lipophilicity or hydrophilicity.

Thus, the following preferred coupling variants are obtained according to the invention:

the therapeutic agent(s) is (are) coupled to the magnetosome or enclosed in the membrane, the therapeutic agent(s) is (are) coupled to the magnetosome or enclosed in the membrane and packed in liposomes, the magnetosome is packed as liposome and this or the therapeutic agents are enclosed in the aqueous interior of the liposomes, therapeutic agents are coupled to the magnetosome or enclosed in the membrane, the magnetosome is packed in liposomes and at least one further therapeutic agent is enclosed in the aqueous or lipophilic interior of the liposomes.

Important therapeutic agents coming into consideration are chemotherapeutic agents such as carboplatin or taxol and radiotherapeutic agents such as yttrium, iodine, technetium or boron. Equally, therapy genes such as suicide genes, antisense oligonucleotides, ribozymes or cytokine genes may be coupled.

The invention allows a broad medical application. The essential advantage of the magnetosomes and magnetoliposomes according to the invention consists in the fact that metastases may be better reached in the body and detected early, their enrichment in the lymphatic vessels is improved blood-brain barriers are better overcome by the new particles which is, in particular, of importance to the detection of Alzheimer plaques and the diagnosis of brain tumours.

Hereinafter the invention is explained in greater detail by means of examples of execution:

1. Obtaining magnetosomes

To obtain magnetosomes in masses the cells of the magnetic bacterium *Magnetospirillum gryphiswaldense* were bred in a 100l fermeter (LP 352, Bioeng. AG) at 30° C. in a culture medium of the following composition (per 1000 ml): 0.3 g of $KH_2PO_4$, 1 g of Na acetate, 1 g of soybean peptone (Merck), 0.1 g of $NH_4Cl$, 0.1 g of yeast extract, pH 6.9. Inoculation was effected by adding 5 l of preculture to 70 l of the medium. Aeration was regulated by stirring and input of compressed air so that the concentration of oxygen in the medium did not exceed 2% of saturation. 70 g of Na acetate and iron sulphate were added to a concentration of 100 µM with the $OD_{400}$=0.55. After approx. 30 hours it was possible to gather magnetic cells.

The cells were centrifugated down and washed. After the cell extract passed the French press three times and was subsequently subjected to a low-run centrifugation it was put into 20 mM HEPES/4 mM EDTA through a magnetic separation column (Miltenyi Biotec). To separate the magnetic particles the column was exposed to the magnetic field of a strong permanent magnet (Sm-Neodyn). This produced a strong inhomogeneous magnetic field in a magnetizable column material for a specific binding of the magnetic particles. The magnetosomes were washed in the column with 20 mM HEPES/200 mM NaCl to remove specifically associated pollution. After having been washed with 20 mM HEPES the magnetosomes were flushed from the column after removing the magnetic field. To separate potentially available membrane contaminations, the magnetosome suspension was applied to a two-layer (50/55% saccharose) sugar gradient and centrifugated in an ultracentrifuge with 25,000 rpm for 25 h. Potentially contained membrane components accumulated at the buffer-saccharose solution interphase whereas the magnetosome particles appeared as pellets on the bottom of the tube. The magnetosomes thus obtained appeared to be electron microscopically pure and showed a distinct lipid and protein pattern.

2. Use of magnetosomes

There were used magnetosomes from *M. gryphiswaldense* with an iron content of 1.35 g Fe/l (determined by means of an atomic absorption spectroscopy (AAS)). The relaxivities were determined by means of a Bruker Minispec pc 120 at 37° C. and 0.47 T as:

$R_1 = 25.503$ mM$-1^*_s-1$ $R_2 = 226.179$ mM$-1^*_s-1$

The relaxivities, in particular $R_2$, are high as compared with various SPIOs (superparamagnetic iron oxide formulations). Only for SPIO-SUVs (small unilamellar vesicles) comparable values were obtained. The following in vivo experiment was carried out: The remaining substance quantity (0.4 ml) was injected in vivo into the tail vein of a male WAG/RIJ (270 g) with a CC531 adenoarcinoma implanted into the liver. Thus, the animal received magnetosomes in a dose of 35.81 $\mu$mol Fe/kg of rat weight. The NMR examination was carried out with a Bruker Biospec BMT 24/40. Thereby, before, immediately after the infection and then at the time indicated in Table 2 nine 3 mm layers and an enclosed external standard tube with the RARE sequence (TR=2500 ms, TE=20 ms, RF=8; NE=8) were taken up through the abdomen of the rat. The signal intensities in the liver and the tumour were measured in four various layers and evaluated. The indicated weakening of the relative signal intensity $SI_{rel}$ is calculated as follows:

$$SI_{rel} = (S_{post\ lip.}/SI_{standard})/(SI_{pre\ lip}/SI_{standard})$$

$SI_{pre\ lip}$ = signal intensity before applying liposomes $SI_{post\ lip}$ = signal intensity after applying liposomes $SI_{standard}$ = signal intensity of the standard.

Already given this comparatively low dose a signal reduction up to 90% was reached in the liver, however in the tumour only weak SI reductions were reached (Table 2). This means that the tumour stands clearly out against the healthy liver tissue (FIG. 1).

TABLE 2

| | tumour mean from all > layers | | | | mean | | liver | | | | mean | mean standard deviation |
|---|---|---|---|---|---|---|---|---|---|---|---|---|
| pre | 1.00 | 1.00 | 1.00 | 1.00 | 1.00 | 0.00 | 1.00 | 1.00 | 1.00 | 1.00 | 1.00 | 0.00 |
| 5 min. | 0.93 | 0.89 | 0.91 | 0.98 | 0.93 | 0.04 | 0.18 | 0.29 | 0.13 | 0.12 | 0.18 | 0.08 |
| 15 min. | 1.00 | 0.96 | 0.98 | 1.02 | 0.99 | 0.03 | 0.19 | 0.35 | 0.10 | 0.13 | 0.19 | 0.11 |
| 31 min. | 1.04 | 0.99 | 0.99 | 1.06 | 1.02 | 0.04 | 0.13 | 0.19 | 0.09 | 0.15 | 0.14 | 0.04 |
| 48 min. | 1.01 | 0.98 | 0.98 | 1.06 | 1.00 | 0.04 | 0.18 | 0.14 | 0.14 | 0.23 | 0.17 | 0.04 |
| 65 min. | 1.00 | 0.98 | 0.98 | 1.13 | 1.02 | 0.07 | 0.24 | 0.18 | 0.14 | 0.13 | 0.17 | 0.05 |
| 82 min. | 0.95 | 0.94 | 0.93 | 1.05 | 0.97 | 0.06 | 0.23 | 0.13 | 0.11 | 0.17 | 0.16 | 0.05 |
| 113 min. | 0.93 | 0.86 | 0.91 | 1.10 | 0.95 | 0.10 | 0.13 | 0.13 | 0.11 | 0.17 | 0.13 | 0.03 |
| 24 h | 0.93 | 0.86 | 0.91 | 1.10 | 0.95 | 0.10 | 0.11 | 0.13 | 0.11 | 0.17 | 0.13 | 0.03 |
| 48 h | 1.05 | 1.00 | 1.02 | 1.14 | 1.05 | 0.10 | 0.11 | 0.12 | 0.12 | 0.11 | 0.11 | 0.01 |
| 110 h | 0.81 | 0.73 | 0.85 | 0.72 | 0.78 | 0.06 | 0.13 | 0.11 | 0.12 | 0.13 | 0.12 | 0.01 |

What is claimed is:

1. A magnetosome having a surface, and comprising a magnetite monocrystal having a maximum diameter of 45 nm surrounded by a phospholipid membrane.

2. A magnetosome of claim 1, wherein said membrane comprises at least one of phosphatidyl ethanolamine, phosphatidyl glycerol, and phosphatidyl choline and containing at least one of palmitic acid, paltitoleinic acid and oleic acid.

3. The magnetosome of claim 1, wherein said membrane comprises 53%±6% phosphatidyl ethanolamine, 38%±6% phosphatidyl glycerol, and 8.9%±5% phosphatidyl choline.

4. The magnetosome of claim 1, in the form of chains of maximum 100 magnetosomes, and having a cationic surface charge.

5. The magnetosome of claim 4, wherein said chains comprise from 10 to 60 magnetosomes.

6. The magnetosome of claim 1, further comprising one or more antibodies.

7. The magnetosome of claim 6, wherein at least one or more of said antibodies is bound to said membrane.

8. The magnetosome of claim 1, wherein the magnetosome is packed within a liposome.

9. The magnetosome of claim 8, wherein said liposome is one of a stealth liposome, a micellar system, an immunoliposome, a cationic liposome, or a fusogenic liposome.

10. The magnetosome of claim 1, further comprising at least one antibody chemically coupled to said surface.

11. The magnetosome of claim 1, further comprising a radionuclide therein.

12. The magnetosome of claim 1, further comprising one or more gene diagnostic agents and a cationic complex for the transfer of genes.

13. A method for preparing the magnetosome of claim 1, which comprises isolating the magnetosome from the magnetic bacterium *Magnetospirillum gryphiswaldense* by fermentation in a culture medium which does not contain complexing agents for iron, the oxygen concentration in the medium being maintained below 2%, adding Na acetate and $FeSO_4$, gathering the magnetic cells, and after lysis of cells recovering the magnetosome by magentic separation of the cell fragments and cell sap.

14. The method of claim 13, wherein said magnetic cells are gathered by centrifuging, and said magnetic separation is carried out in a magnetic separation column.

15. The method of claim 14, wherein said magnetic separating column employs a samarium/neodymium permanent magnet.

* * * * *